United States Patent [19]

Baldeschwieler et al.

[11] Patent Number: 4,581,222

[45] Date of Patent: Apr. 8, 1986

[54] MEMBRANE IMMUNE ASSAY

[75] Inventors: John D. Baldeschwieler; Ronald C. Gamble, both of Pasadena; Albert M. Lin, Walnut; George W. Tin, Arcadia, all of Calif.

[73] Assignee: California Institute of Technology, Pasadena, Calif.

[21] Appl. No.: 465,360

[22] Filed: Feb. 9, 1983

[51] Int. Cl.[4] .................... A61R 49/00; A61K 43/00; G01N 33/54; G01T 1/00
[52] U.S. Cl. ........................................ 424/1.1; 424/9; 436/517; 436/537; 436/804; 436/827
[58] Field of Search ..................... 424/1.1, 9; 436/517, 436/537, 804, 829

[56] References Cited

U.S. PATENT DOCUMENTS 4,310,506  1/1982  Baldeschwieler et al. .......... 424/1.1

OTHER PUBLICATIONS

Hwang et al., Proc. Nat. Acad. Sci. USA, 74 (1977) 4991-5.
Mangold et al., Fed. Proc., 37 (1978) 1279.
Martin et al., Chem. Abstracts, 89 (1978) #211221y.
Parce et al., Proc. Nat. Acad. Sci. USA, 75 (1978) 1515-8.

*Primary Examiner*—Christine M. Nucker
*Attorney, Agent, or Firm*—Joseph E. Mueth

[57] ABSTRACT

An immunoassay method for detection of antigen is disclosed. The method employs complement mediated lysis of vesicles loaded with In-111 or other gamma-emitting cation, and quantitative detection of the lysis by gamma-ray perturbed angular correlation (PAC) spectroscopy. The vesicles are labeled with a substance competitive to the antigen to be measured, and the concentration of the antigen in the sample measured by assessing the diminution in lysis due to the presence of the competing antigen.

The method may also be used to assess the immunologic competence of a subject by injecting suitably sensitized vesicles and monitoring the in vivo lysis pattern by (PAC).

20 Claims, 4 Drawing Figures

MEMBRANE IMMUNE ASSAY

BACKGROUND OF THE INVENTION

The invention herein relates to measurement of the concentration of antigenic substances, most usually in biological fluids, and to assessing the immunologic competence of a subject organism. More specifically, the invention employs perturbed angular correlation spectroscopy (PAC) to monitor the interaction of antibody/antigen-sensitized vesicles loaded with a gamma-emitting cation with antibodies for the subject antigen/antibodies.

Techniques for immunoassay of specific substances have undergone extensive expansion in the last 10 to 15 years. The concentration of antigen is most commonly sought in biological fluids, for example, blood, urine and spinal fluid, although there is no theoretical reason why antigen concentration could not be measured in the context of any fluid medium, biological or not. Radio immunoassay (RIA) is an extremely sensitive and reasonably specific technique and has found a large scope of use (Thorell et al 1978); however, it requires separation of bound from unbound antigen in order to assess the results. Spin immunoassay (SIA) has also been employed (Leute, et al. 1972, Hsia et al 1973, Wei et al. 1975); it obviates the need for separation, but is relatively insensitive. An additional technique, using enzyme mediated reactions as the measure of the extent of the antigen-antibody reaction has also recently been employed. Again, ordinarily, separation of the bound material is required, although this is not always the case. The present invention, as employed in the measurement of the concentration of the antigenic substances, offers a method with sensitivity comparable to RIA, which does not require separation of the bound antigen.

In addition to measurement of antigen concentration, there is considerable interest in determining the general competence of the immune system of an organism. This is desirable, for example, in order to assess the effects of various environmental conditions on the immune system (Tengerdy, et al. 1972, 1973; Bramen, et al. 1973; Thomas, et al. 1973; Nulsen, et al. 1974; Kripke, et al. 1976). In addition, it is frequently desirable deliberately to manipulate the immune system, and to monitor these manipulations. Protocols and drugs are, for example, employed to immunosuppress recipients of organ transplants to prevent rejection (Maugh, 1980; Trotta, et al. 1981) and thus it is necessary to measure the effectiveness of suppressing immune response. Conversely, assays of immunological competence are necessary to assess the effectiveness of attempts to potentiate the immune system, employing, for example, adjuvants which may help control malignant growth (Schnipper, et al. 1980; Taniguchi, et al. 1981). The present method, in view of its ability to quantify immunological response, is an aid in designing and administering these drugs and protocols which affect the immune system.

The present invention takes advantage of the ability of complement to mediate the lysis of liposomes sensitized with antigen that bind to antibody.

It is known that liposomes loaded with a complexed gamma-emitting cation, usually In-111 linked to a chelator such as nitrilotriacetic acid (NTA) can be assayed for integrity by the use of perturbed angular correlation spectroscopy, (PAC), which generates a factor related to the tumbling rate of the gamma emitter. When the gamma emitter is enclosed in the vesicle, the tumbling rate is greater than when it is freed into a biological fluid, because of the ability of the gamma-emitting cation to associate itself with other proteins found in the fluid. The tumbling frequency is thereby slowed. Accordingly, it has been shown that PAC can be used as a measure of the extent of lysis of liposomes containing such gamma emitters. See, for example, Mauk, M. R. and Gamble, R. C. Proc. Natl. Acad. Sci. (USA) 76: 765-769 (1979).

In the present invention, this technique is used to follow that lysis of the "sensitized" vesicles which is due to specific binding of the vesicle containing an antigenic surface to the antibody correlated with it. When such binding occurs, complement mediates lysis. Accordingly, this technique serves as a method to assess the antigen-antibody reaction in any suitable context.

SUMMARY OF THE INVENTION

Briefly, the present invention comprises a method of determining the concentration of an antigenic substance in a sample, which method comprises mixing together:
 (a) the sample;
 (b) antibody to said antigenic substance;
 (c) vesicles loaded with a gamma-emitting cation, and including on their surface an entity competitive with the antigenic substance for the antibody; and
 (d) complement; and measuring the time integrated pertubation factor, $G_{22}(\infty)$, associated with the gamma-emitting cation.

The invention also comprises a method for measuring the concentration of an antigenic substance in a sample, which method comprises:
 (a) mixing the sample with gamma-emitting cation loaded, antigen-sensitized vesicles, antibody to the antigenic substance, and complement; and
 (b) measuring the time integrated pertubation factor $G_{22}(\infty)$ associating with the gamma-emitting cation.

Still further the invention comprises a method for determining the immunological response in vivo in a subject vertebrate, which method comprises:
 (a) injecting a subject vertebrate with antigen sensitized vesicles loaded with a gamma-emitting cation; and
 (b) measuring the time integrated pertubation factor for the gamma-emitting the cation.

In one aspect, the invention relates to a method of measuring the concentration of an antigenic substance in a fluid sample commonly a biological fluid. In the method, the antigenic substance in the sample will be allowed to compete with sensitized vesicles for binding with the appropriate antibody. The vesicles contain a gamma-emitting cation, so that the extent of disruption of the vesicles may be measured by applying perturbed angular correlation spectroscopy to measure the tumbling rate of the gamma emitting cation. In biological fluids, encapsulated cations have higher tumbling rates than those which are released into the surrounding fluids. The higher the concentration of the antigenic substance in the sample to be assayed, the more successful it will be in preventing the binding of the sensitized vesicles to antibody and thus in preventing the relase of the gamma emitting cation into solution. Thus, the magnitude of the decline in tumbling rate will depend on the ability of the measured antigen to prevent the disruption of the sensitized vesicles.

Accordingly, in this aspect, the invention comprises mixing, with the sample to be analyzed: (1) vesicles loaded with a gamma-emitting cation, and sensitized with a substance competitive with the antigenic substance to be measured; (2) antibody to the antigen to be measured, and (3) complement.

The extent of change in the time integrated pertubation factor ($G_{22}(\infty)$) as measured by PAC is then a measure of the amount of antigen present in the sample.

In another aspect, the invention concerns a method for assessing the immunological response of a subject vertebrate organism by utilizing the ability of the antibodies formed by the subject system to precipitate the lysis of the above-described labeled vesicles.

The advantages of the method of the present invention are several fold. It is sensitive, specific, and does not require separation of bound and unbound antigen. It can be applied in vivo, and is relatively non-invasive, in that it requires the injection of only small amounts of label, and does not require the withdrawal of appreciable samples of the subject's own fluids.

DESCRIPTION OF THE PREFERRED EMBODIMENTS

Figure 1:
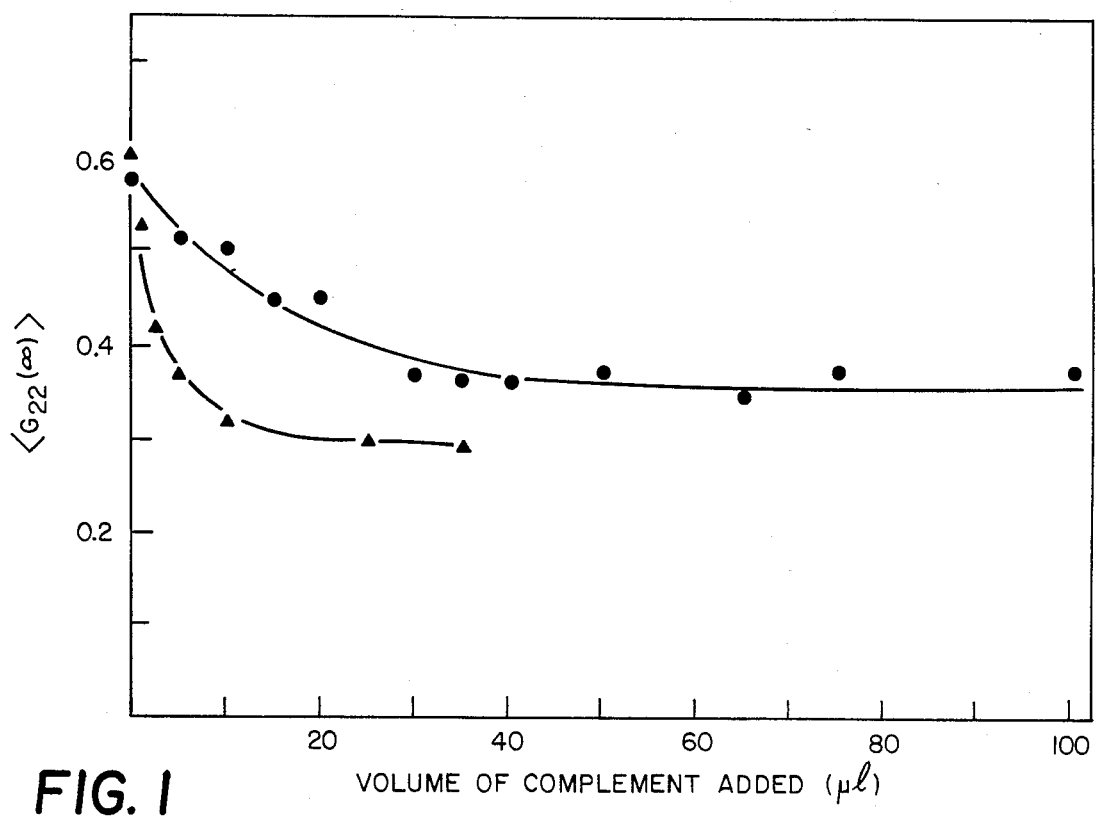

As used herein, "gamma-ray perturbed angular correlation spectroscopy (PAC)" refers to a technique which utilizes a gammaray coincidence spectrometer to monitor changes in the rotational correlation time of a gamma emitter by measuring a "time integrated pertubation factor", $G_{22}(\infty)$. This technique is described by Meares, C. F., et al. *Proc. Natl. Acad. Sci.*, 69: 3718 (1972), incorporated herein by reference. The $G_{22}(\infty)$ value is high when a high tumbling rate is experienced by the measured species, and decreases as the tumbling rate diminishes.

"Antigen" includes substances which are capable of eliciting an antibody response, and substances which bind to the antibodies formed. It is understood that while antibody response may be elicited by a macromolecule, the entire surface of this molecule may not be required for binding to occur. "Antigen" here includes both the binding site above, and the entire hapten.

"Vesicles" refers to liposomes which are constructed by standard means known in the art from phospholipids, and other components appropriate to the particular usage intended. Means of constructing both large unilamellar vesicles (LUV) and small unilamellar vesicles (SUV) are well-known in the art. SUVs may be constructed, for example, by the method of Mauk, M. R. et al, *Proc. Natl. Acad. Sci.*, 76: 765 (1970), incorporated herein by reference, by probe sonication of a lipid mixture containing, for example, distearoyl phosphatidylcholine (DSPC) and cholesterol in phosphate buffered saline. LUVs may be prepared for example, according to the method of Deamer, D. et al, *Biochem. Biophys. Acta* 443: 629 (1976), incorporated herein by reference. In this method, the DSPC: cholesterol mixture is dissolved in an ether-ethanol mixture and aspirated into an aqueous solution with an infusion pump.

Preferably the walls of the unilamellar vesicles are self-aligned layers of L-α-disteraroyl phosphatidylcholine and/or L-α-dipalmitoyl phosphatidylcholine or similar lipid substances. The walls of the vehicles can also be formed from soybean phospholipid, egg yolk lecithin and L-α-dimyristoyl phosphatidylcholine.

Cholesterol, various carbohydrate analogues of cholesterol, and other additives can also be added to the phospholipid vesicle walls. For example, L-α-phosphatidyl ethanolamine, L-α- phosphatidyl-L-serine, dicetyl phosphate, and stearylamine. An ionophore is also present in the vesicle wall.

"Sensitized vesicles" refers to vesicles which incorporate into their construction a substance which is competitive with the antigen to be measured for antibody, i.e. which incorporate an antigenic substance at their surface. Such sensitized vesicles are constructed, as more particularly set forth hereinbelow, by including in the initial construction mixture, besides the basic structural phospholipid, a small percentage of the sensitizing substance or antigen.

"Loaded" vesicles refers to vesicles which have enclosed, within the envelope they create, a material which will be released if the envelope is broken. In the context of the present invention, vesicles are typically loaded with a gamma-emitting cation, preferably Indium-111, which is preferably bound to a chelating agent. The material to be loaded is conventionally either included in the reaction mixture from which the vesicles are originally formed or is subsequently added and incorporated by the already formed vesicles. This process is frequently aided by the presence in the vesicles of an ionophore.

The chelator within the vesicle preferably is nitrilotriacetic acid (NTA). However, other chelators for the cations may be used. Where the cations are polyvalent metal ions, polyamino carboxylic acid chelators for such ions may be employed, such as ethylenediaminetetraacetic acid (EDTA), diethylenetriaminepentaacetic acid, diaminocyclohexanetetraacetic acid and iminodiacetic acid.

The cations should be radioactive tracers with two gamma rays emitted in succession, desirably bivalent or trivalent, for example, $^{111}$In.

In addition to the ionophore mentioned above, ionophores generally are useful, and include polyethers:- lasalocid A (X-537A), 5-bromo derivative of lasalocid; cyclic depsipeptides: beauvericin; cyclic peptides: DECYL-2 and valinomycin; and antifungal toxins:avenaciolide.

The preferred ionophore (a generic term intended to imply compounds which are ion-loving or ion attracting) [6S-[6α(2S*, 3S*), 8β(R*),9β(R*),9β, 11α]]-5-(methylamino)-2-oxo-2-(1H-pyrrol2-yl)ethyl]-1,7-dioxaspiro[5.5]undec-2yl]methyl]-4-benzoxaxolecarboxylic acid, hereinafter referred to as ionophore A23187, has been used to complex and carry divalent cations across natural and artificial lipid membranes, Hyono, A., Hendriks, Th., Daemen, F. J. M., and Bonting, S. L. (1975) Biochim. Biophys. Acta., 389, 34–46; Sarkadi, B., Szasz, I., and Gardos, G. (1976) *J. Membrane Biol.* 26, 357–370; LaBelle, E. F. and Racker, E. (1977) *J. Membrane Biol.*, 31, 301–315; Pfeiffer, D. R. Taylor, R. W. and Lardy, H. A. (1978) *Ann. N. Y. Acad. Sci.*, 307, 402–423. Evidence also exists that A23187 can form complexes with trivalent cations, e.g., $La^{+3}$, Pfeiffer, D. R., Reed, P. W., and Lardy, H. A. (1974) Biochemistry, 13, 4007–4014.

METHOD OF THE INVENTION

A. Determining Concentration of Antigenic Substance in Biological Fluid

In the aspect of the invention which utilizes complement mediated lysis to measure the concentration of an antigenic substance, biological fluids are withdrawn and measured in vitro.

Biological fluids which are acceptable for use as samples for such measurements include, for example, blood, serum, urine, spinal fluid, or even less frequently measured fluids such as saliva, or gastric juices. The source of such fluids may be any organism which produces fluids which contain, possibly, the substance sought to be analyzed. Accordingly, the organism may be vertebrate or invertebrate, plant or animal, although the most important applications, of course, apply to vertebrates. In addition, the method can be used with respect to fluids of non-biological origin, so long as additional protein or other binding agents are supplied which will have the effect of decreasing the tumbling rate of the gamma-emitting cation released from the vesicles during the assay. Thus, a plain aqueous solution may be used, if, for example, serum albumin is added so as to provide such a binding agent.

In the method of the invention, the antigenic substance to be measured will be determined by its ability to compete for antibody with sensitized vesicles containing the gamma emitting label. Accordingly, vesicles must be constructed which contain in their surface, molecules which are competitive for antibody with this antigenic substance. Ordinarily, the antigenic substance, itself, would be incorporated into the vesicles in making this construction. For example, N-2, 4-dinitrophenyl-E-amino caprolate (DNP-cap) is an antigenic substance whose concentration can be measured. In that case, the vesicles would be sensitized by utilizing in their construction, E-dinitrophenyl amino-caproyl phosphoethanolamine (DNP-cap-PE). The DNP-cap will thereby be incorporated into the surface of the vesicles. The vesicles and the antigen will thus be attracted into the same antibody.

Antibodies can be obtained in a variety of ways. Ordinarily, these are obtained by producing antiserum to the antigen to be measured using mice or rabbits. Often, such antisera are commercially available for commonly encountered antigens. Further refinements can, of course, be made in particular cases by, for example, preparing monoclonal antibodies entirely specific to the desired antigen. These techniques are known in the art, and are applicable to the present method.

Complement may be obtained from any appropriate vertebrate source and is also generally commercially available. For example, guinea pig complement can be obtained from GIBCO.

In the method of the invention, a small quantity of sample is mixed with appropriately sensitized vesicles, appropriate antibodies, and complement. Ordinarily, vesicles, antibody, and complement are added in sequence, although any order is satisfactory. If the sample to be tested does not have sufficient cation binding materials contained in it, additional such materials in the form, for example, of serum albumin must also be added. The $G_{22}(\infty)$ is measured after incubation has effected lysis of the vesicles. Appropriate conditions of pH and salt concentration must also be maintained.

In a typical assay, a few microliters of heat inactivated serum (if binders are lacking in the sample), a similar quantity of vesicles, antibody-containing serum, and guinea pig complement are added in sequence. The solution is incubated for about ten minutes to one hour at about 30° to 40°, and the value of $G_{22}(\infty)$ determined by PAC spectroscopy. The incubation conditions, will, of course, vary with the specific assay used, however, in general it is found that approximately 37° C. or biological temperature, is desirable, and the lysis takes place within approximately thirty minutes.

The lysis of the loaded sensitized vesicles can be confirmed by subsequent addition of isopropanol to test the complete lysis of any remaining vesicles to provide a control standard against which the measured $G_{22}(\infty)$ can be compared.

B. In vivo Assessment of the Immune System

Due to the use of a high-energy gamma-ray radiocation and the highly sensitive spectroscopy for monitoring the tumbling rate of radiocation in different environments, the assay could also be used to assess immunological responsivenes in vivo. Visicle sensitized with antigen can be injected directly in vivo in the presence of antibodies, complement will mediate the lysis of the vesicles in circulation. This releases the encapsulated radiocation which will immediately bind to the circulating protein. This binding will slow down the tumbling rate of the radiocation and decrease $G_{22}(\infty)$ as monitored by PAC spectroassay. This change in $G_{22}(\infty)$ can be used to quantify the amount of antibodies present in the system.

The following examples are intended to illustrate but not limit the invention:

PREPARATION A

Preparation of DNP-cap Sensitized LUVs

20 μmole DSPC, 12.5 μmole of cholesterol, 0.1 μmole of A-23187 (a commercially available ionophore) and 0.2 μmole DNA-cap-PE were dissolved in 16 ml ether-ethanol (4:1 by volume). The lipid solution was aspirated in a glass syringe into the aqueous phase at 0.25 ml per minute with the aid of an infusion pump (Sage instruments). The aqueous phase consisted of 4 ml phosphate saline buffer (PBS) pH 7.4, and 10 mM nitrolotriacetic acid (NTA) and was maintained at 80° C. At the conclusion of the injection, the vesicle suspension was removed and filtered through a 1.0 μm nucleopore polycarbonate filter. The NTA external to these vesicles was then removed by column chromatography using Sephadex G-50.

PREPARATION B

Preparation of Loaded Sensitized Vesicles 0.1 mg of the vesicles as prepared in Preparation A were incubated with $InCl_3$ at 80° C. for 45 minutes. Much of the In-111 was incorporated into the vesicles, but any remaining In-111 was subsequently complexed to EDTA and separated from the loaded vesicles by chromatographing the mixture on a Sephadex G-50 column equilibrated with PBS.

PREPARATION C

Vesicles Prepared for the Process of the Invention

Using the procedure set forth in Preparation A, the following vesicles were prepared; the amounts given are mole ratios:

| Abbreviation | DSPC | Chol | A-23187 | DNPcap-PE |
| --- | --- | --- | --- | --- |
| LUV/24 | 2 | 1.25 | .005 | .024 |
| LUV/12 | 2 | 1.25 | .005 | .012 |
| LUV/9 | 2 | 1.25 | .005 | .009 |
| LUV/4 | 2 | 1.25 | .005 | .004 |
| LUV/0 | 2 | 1.25 | .005 | 0 |
| LUV/20 | 2 | 1.25 | .1 | .020 |
| LUV/10 | 2 | 0.20 | .005 | 0.02 |
| SUV | 2 | 1.0 | 0.004 | 0.024 |

EXAMPLE I

Measurement of Complement Mediated Lysis Using PAC

In a 10×75 mm glass tube, 100 μl of heat inactivated calf serum, 50 μl of vesicles prepared in Preparation C and loaded as described in Preparation B, various amounts of anti-DNP-cap antiserum, and guinea pig complement were added in sequence. The solution was then brought to a total volume of 20 μl with a solution of 0.15M NaCl, 1 mM MgCl$_2$, and 0.15 mM CaCl$_2$, pH 7.4. After thirty minutes of incubation at 37° C., the G$_{22}(\infty)$ values were determined, with results as shown below.

Finally, all samples were treated with isopropanol to lyse any remaining vesicles and the G$_{22}(\infty)$ redetermined.

| | Results | | |
|---|---|---|---|
| | | G$_{22}(\infty)$ | |
| Sample | no serum | serum, measured after 30 min. 37° | serum + isopropanol |
| Free $^{111}$IN-NTA Complex | 0.70 | 0.19 | 0.18 |
| $^{111}$IN-NTA complex loaded: | | | |
| LUV/10 | 0.59 | 0.45 | 0.20 |
| LUV/20 | 0.62 | 0.60 | 0.20 |
| SUV | 0.61 | 0.59 | 0.24 |

As seen from these results, free In-111 binds to serum with appreciable lowering of G$_{22}(\infty)$. This is evident also from column 3, where isopropanol has freed all In-111 from the vesicles. The lowered values after incubating with serum present indicates partical release from the vesicles.

EXAMPLE II

Effect of Variables

Incubations were carried out generally as set forth in Example I, with the moficiations below. The G$_{22}(\infty)$ consistently were measured after thirty minutes at 37° C.

A. LUVs treated with 5 μl of anti-DNP-cap antiserum; and SUVs treated with 25 μl of anti-DNP-cap antiserum were incubated as in Example I with varying amounts of complement. FIG. 1 shows the results of varying the amount of complement from approximately 2 μl to 100 μl of complement. It appears that 40 μof complement is sufficient to maximize the lytic effect under these conditions.

Figure 2:
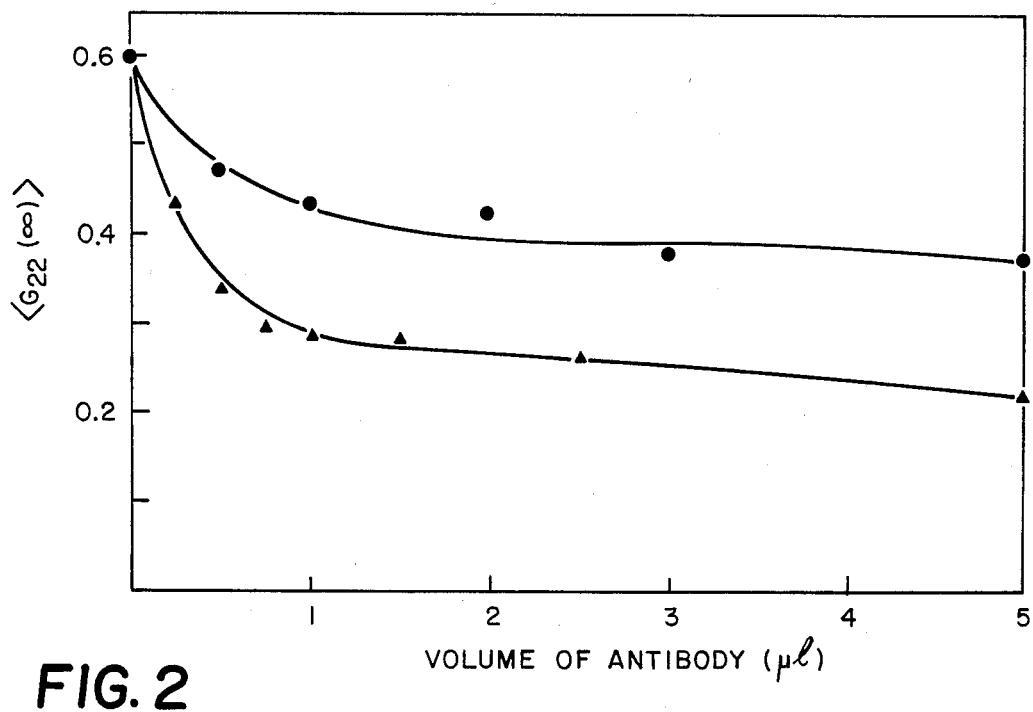

B. In a different experiment, LUVs treated with 20 μl of complement and SUVs treated with 50 μl of complement were incubated with varying volumes of antibody up to 5 μl. Apparently, under these conditions, 2 μl of antibody was sufficient to obtain the desired results. These results are shown in FIG. 2.

Figure 3:
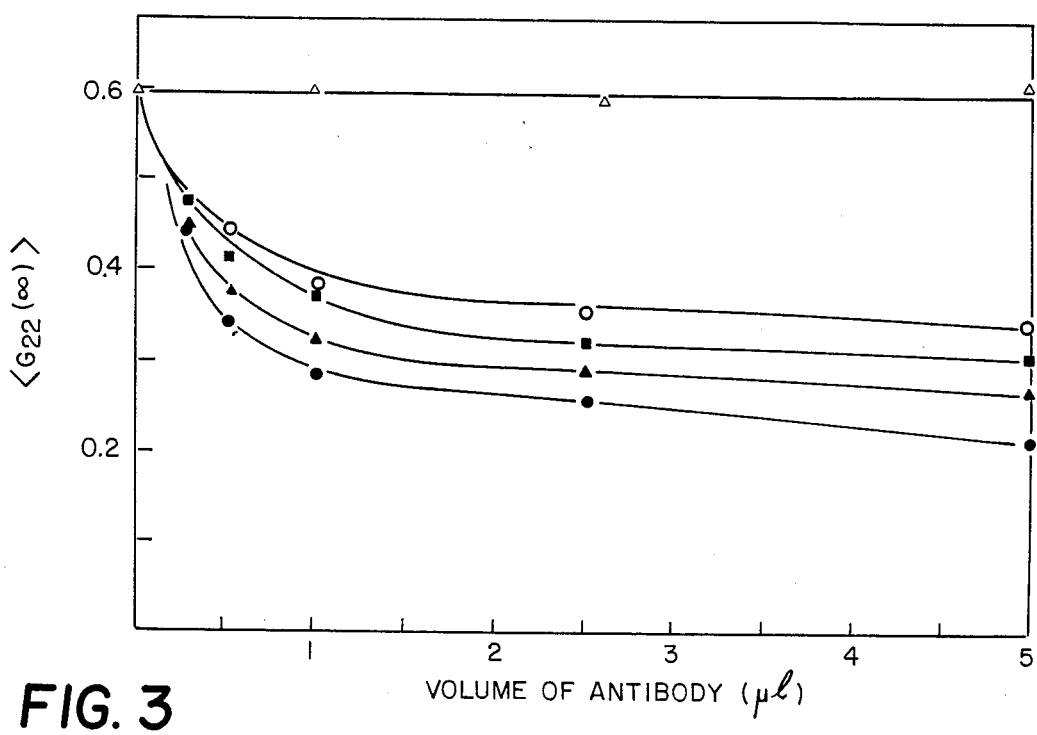

C. In a third experiment, LUVs with varying DNP cap-PR concentrations, incubated with 20 μl of complement were used. The volume of antibody required under these circumstances appears to be sufficient, regardless of the composition of the vesicle, at approximately 1 μl of added antibody. These results are shown in FIG. 3.

EXAMPLE III

Calibration of the antigen concentration measurement

Figure 4:
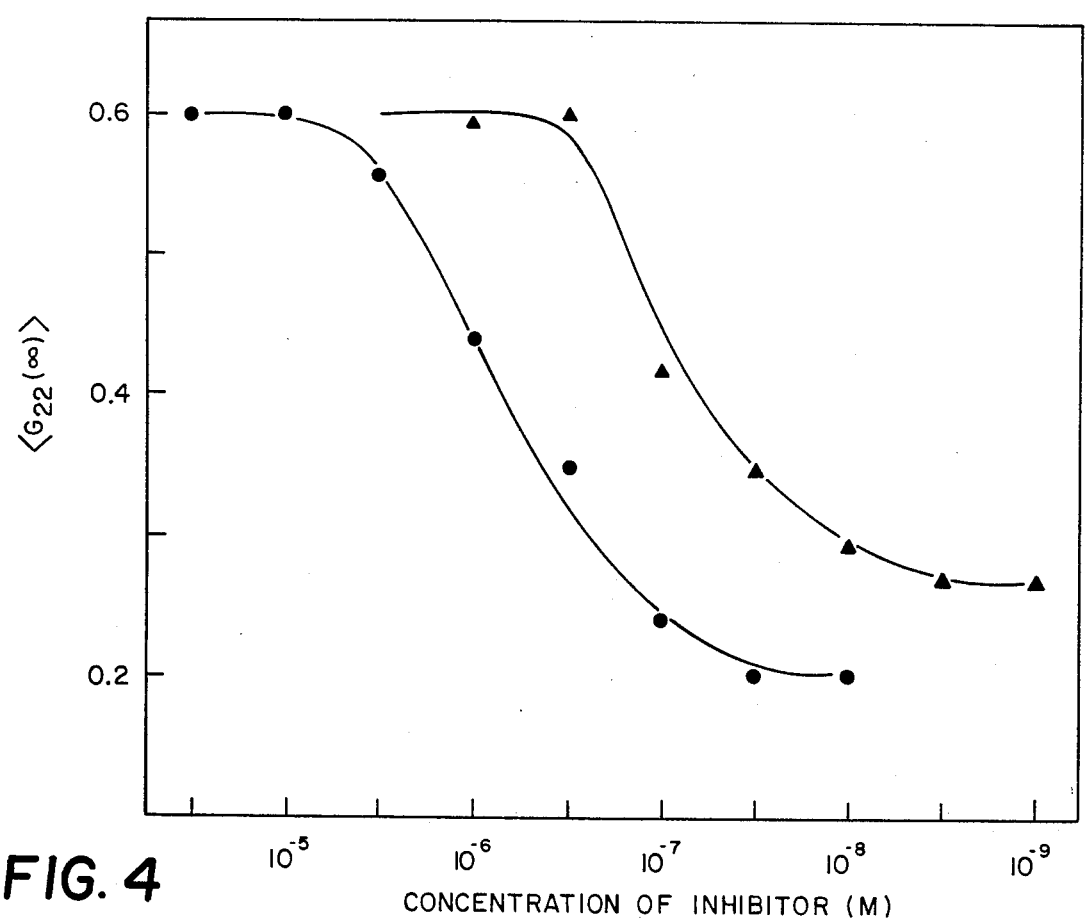

Incubation was carried out as set forth in Example I using LUV/24 with samples of DNP-cap concentration of 10$^{-5}$M to 10$^{-9}$M approximately. As shown in FIG. 4, 50% inhibition occurred in the range of 10$^{-7}$ concentration of the antigen, when 5 μl or 0.75 μl of antibody was employed.

Having fully described the invention, it is intended that it be limited solely by the lawful scope of the appended claims.

We claim:

1. A method for determining the concentration of an antigenic substance in a sample, which method comprises mixing together:
   (a) the sample;
   (b) antibody to said antigenic substance;
   (c) vesicles loaded with a gamma-emitting cation, and including on their surface an entity competitive with the antigenic substance for the antibody; and
   (d) complement; and
measuring the time integrated pertubation factor associated with the gamma-emitting cation.

2. The method of claim 1 wherein the gamma-emitting cation is indium-111.

3. The method of claim 1 wherein the entity competitive with the antigen for antibody is the same entity as the antigen.

4. The method of claim 1 wherein the vesicles are large unilamellar vesicles (LUV).

5. The method of claim 1 wherein the antibody and complement are derived from the same species of organism.

6. The method of claim 1 wherein the mixture is incubated for between 15 minutes and 30 minutes before measuring the time integrated pertubation factor.

7. the method of claim 1 wherein the time integrated pertubation factor is measured as a function of time.

8. The method of claim 1 which includes a step comprising constructing a control by mixing loaded sensitized vesicles, antibody, and complement, determining the time integrated pertubation factor and comparing this time integrated perturbation factor to that of an analogous mixture which includes sample.

9. A method for measuring the concentration of an antigenic substance in a sample, which method comprises:
   (a) mixing the sample with gamma-emitting cation loaded, antigen-sensitized vesicles, antibody to the antigenic substance, and complement; and
   (b) measuring the time integrated pertubation factor associated with the gamma-emitting cation.

10. The method of claim 9 wherein the gamma-emitting cation is indium-111.

11. The method of claim 9 wherein the entity competitive with the antigen for antibody is the same entity as the antigen.

12. The method of claim 9 wherein the vesicles are large unilamellar vesicles.

13. The method of claim 9 wherein the antibody and complement are derived from the same species of organism.

14. The method of claim 9 wherein the mixture is incubated for between 15 minutes and 30 minutes before measuring the time integrated pertubation factor.

15. The method of claim 9 wherein the time integrated pertubation factor is measured as a function of time.

16. The method of claim 9 which includes a step comprising constructing a control by mixing loaded sensitized vesicles, antibody, and complement, determining the time integrated perturbation factor and comparing this time integrated pertubation factor to that of an analogous mixture which includes sample.

17. A method for determining the immunological response in vivo in a subject vertebrate, which method comprises:

(a) injecting a subject vertebrate with an antigen sensitized vesicles loaded with a gamma-emitting cation; and (b) measuring the time integrated pertubation factor for the gamma-emitting the cation.

18. The method of claim 17 wherein the gamma-emitting cation is indium-111.

19. The method of claim 17 wherein the vesicles are large unilamellar vesicles.

20. The method of claim 17 wherein the time integrated pertubation factor is measured as a function of time.

* * * * *